United States Patent

Acciai et al.

[11] Patent Number: 5,855,802
[45] Date of Patent: Jan. 5, 1999

[54] METHOD AND APPARATUS FOR FORMING A TUBULAR ARTICLE HAVING A PERFORATED ANNULAR WALL

[75] Inventors: Michael Acciai, Newark Valley; Richard Ronald Hall, Endwell, both of N.Y.

[73] Assignee: International Business Machines Corporation, Armonk, N.Y.

[21] Appl. No.: 675,457

[22] Filed: May 30, 1996

[51] Int. Cl.[6] .................................. B44C 1/22; C23F 1/02
[52] U.S. Cl. ............................ 216/8; 216/56; 216/48; 216/94; 156/345; 156/659.11; 623/1
[58] Field of Search ................................. 216/8, 56, 94, 216/48; 623/12; 156/345

[56] References Cited

U.S. PATENT DOCUMENTS

| | | | |
|---|---|---|---|
| 5,139,480 | 8/1992 | Hickle et al. | 604/8 |
| 5,197,978 | 3/1993 | Hess | 623/1 |
| 5,266,073 | 11/1993 | Wall | 623/1 |
| 5,269,882 | 12/1993 | Jacobsen | 156/659.1 |
| 5,344,426 | 9/1994 | Lau et al. | 606/198 |
| 5,395,718 | 3/1995 | Jensen et al. | 430/595 |

*Primary Examiner*—R. Bruce Breneman
*Assistant Examiner*—Michael E. Adjodha
*Attorney, Agent, or Firm*—Schmeiser, Olsen & Watts; Lawrence R. Fraley

[57] ABSTRACT

A method for forming a tubular article having a perforated annular wall, such as a surgical stent, includes coating the exterior and interior cylindrical surfaces of a tubular member with a photoresist, exposing selected portions of the photoresist coated surfaces to light, developing the coating, and then etching the coating to remove unexposed portions of the coating and immediate underlying portions of the annular wall, thereby forming a tubular article having a wall structure defined by a skeletal framework. An apparatus for exposing a light-sensitive coating to a tubular article includes means for rotating and translating the article with respect to a light source, along a longitudinal axis and simultaneously exposing aligned portions of the interior and exterior cylindrical surfaces of the tubular member. The method and apparatus embodying the present invention are particularly suitable for forming stents that support the walls of weak human arteries.

9 Claims, 3 Drawing Sheets

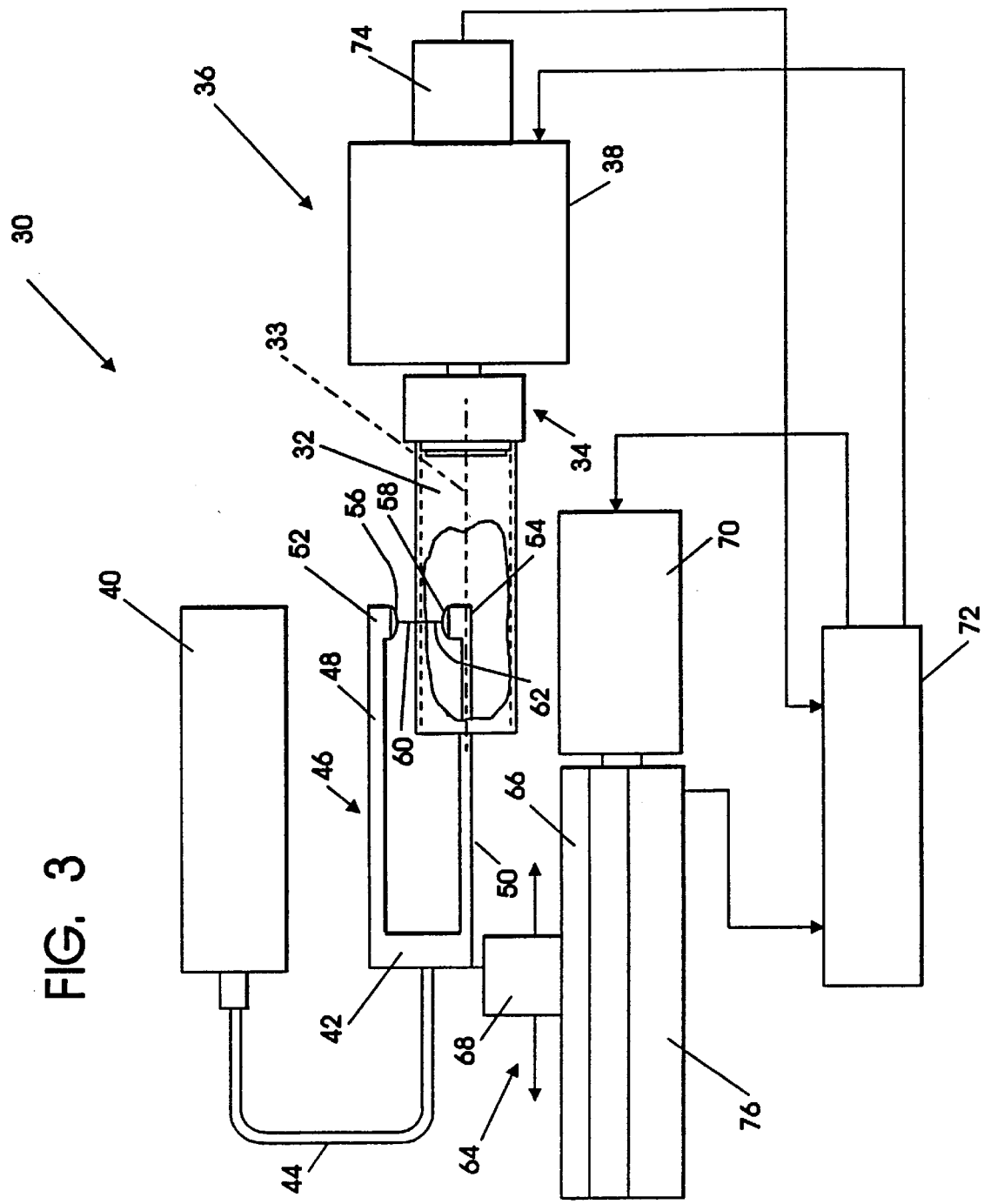

METHOD AND APPARATUS FOR FORMING A TUBULAR ARTICLE HAVING A PERFORATED ANNULAR WALL

BACKGROUND OF THE INVENTION

1. Technical Field

This invention relates generally to a method and apparatus for forming a tubular article having a perforated annular wall, and more particularly to a method and an apparatus useful in the manufacture of stents.

2. Background Art

A stent is a relatively new device that supports the walls of weak human arteries. Heretofore, stents have been difficult and costly to fabricate. Typically, stents are formed from tantalum or stainless steel wire that is formed into complex helical shapes. The shapes of commercially available stents require very high levels of plastic deformation of the wire in a die, which work hardens the metal. The formed helical shape is typically maintained by strategically placed, welded joints. The high, localized heating and cooling of the welding process recrystallizes the wire, causing further damage to the wire's material.

Medical stents require flexibility in a bending mode during insertion, as well as torsional and radial stiffness to provide support to the artery wall. Typically, a stent is inserted over an angioplasty balloon and compressed to form a wire mesh sleeve. The balloon and stent sleeve assembly is then inserted into a patient's artery and moved to a desired position. After proper positioning, the balloon is expanded and thereby the stent is permanently enlarged within the artery wall, after which the balloon is withdrawn and the stent retained within the artery. Generally, the stent attaches to the walls of the artery and is exposed to repetitive loading and unloading as it is flexed with the artery walls as a permanent part of a patient's circulatory system.

The present invention is directed to overcoming the problems set forth above. It is desirable to have a stent produced by a method that does not require high deformation rates nor welding, nor other forming processes that would adversely affect the material properties of the stent. It is also desirable to have a method of manufacture for medical stents that does not cause high levels of residual stress in the formed stent. It is also desirable to have the such a method, supported by a suitable apparatus, that is easily automated and controllable.

SUMMARY OF THE INVENTION

In accordance with one aspect of the present invention, a method for forming a tubular article having a perforated annular wall includes initially providing a tubular member having a solid annular wall defined by exterior and interior cylindrical surfaces. The exterior and interior cylindrical surfaces of the tubular member are coated with a photoresist. Selected portions of the coated surface are exposed to light, after which the coating is developed and then etched to remove unexposed portions of the coating and the immediate underlying portions of the solid annular wall. During etching, voids are formed in the unexposed portions of the annular wall, thereby forming a tubular article having a wall structure defined by a skeletal framework. Other features of the method for forming a tubular article, embodying the present invention, include chemically deburring the skeletal framework.

In accordance with another aspect of the present invention, an apparatus for exposing a light-sensitive coating applied to a tubular article having exterior and interior cylindrical surfaces and spaced ends, includes a means for rotatably supporting the tubular member and a means for rotating either the tubular member or a light source about a predetermined longitudinal axis. The apparatus also includes a laser, a beam splitter in optical communication with the laser, and a bifurcated optical guide in optical communication with the beam splitter. The bifurcated optical guide has one arm that extends along the longitudinal axis and is positioned adjacent the exterior cylindrical surface of the tubular member when the tubular member is rotatably supported in the apparatus. The second arm of the bifurcated optical guide also extends along the longitudinal axis and is positioned adjacent the interior cylindrical surface of the tubular member when the member is rotatably supported in the apparatus. Each of the arms of the optical guide has a head portion that is aligned with each other and is adapted to transmit a respective beam of laser energy from the beam splitter to the head portion. A lens is disposed at each of the head portions of the arms of the bifurcated optical guide, and each of the lenses is constructed to focus a respective beam of laser energy onto the respective adjacently disposed cylindrical surface of the tubular member when the member is rotatably mounted in the apparatus. The apparatus further includes a means for moving either the tubular member or the bifurcated optical guide along the longitudinal axis.

Other features of the apparatus embodying the present invention include a controller that is operatively connected to the means for rotating the tubular member about a longitudinal axis and to the means for moving the bifurcated optical guide along the longitudinal axis.

BRIEF DESCRIPTION OF THE DRAWINGS

FIG. 3 is a schematic diagram of the apparatus, embodying the present invention, for exposing a light sensitive coating.

DETAILED DESCRIPTION OF A PRESENTLY PREFERRED EXEMPLARY EMBODIMENT

The method for forming a tubular article having a perforated annular wall, in accordance with the present invention, eliminates processes that cause high levels of residual stress in the formed article. The perforated-wall tubular article is manufactured in a manner similar to that used to form high definition electronic circuitry on substrates. Briefly, a cylinder of metal, or other suitable material, is coated with photoresist, and an art work generator is then used to expose the coated surfaces to form a desired, respectively aligned, rib pattern on both the inner and outer cylindrical surfaces of the cylinder. The cylinder is then chemically etched to form a mesh tube that is useful for arterial support, or other use. Also, in accordance with the present invention, an apparatus is provided for exposing a light-sensitive coating applied to both interior and exterior cylindrical surfaces of the tubular article. The apparatus includes a light source, e.g., a laser, that produces a beam that is passed through a beam splitter that divides the beam into two segments. The two beams respectively pass along two arms of an optical guide that are disposed parallel to the interior and exterior surfaces of the tubular article. The tubular article is mounted on a mandrel which is rotated simultaneously with linear movement of the optical guide with respect to the tubular article.

Figure 1:
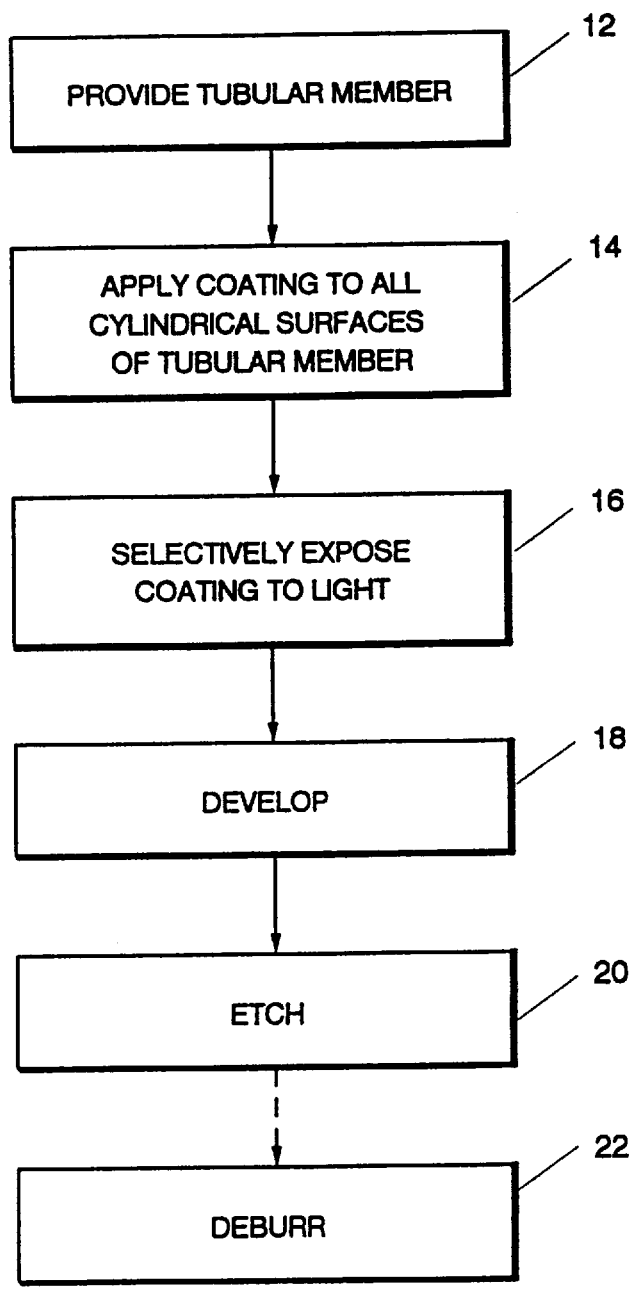
FIG. 1 is a flow diagram illustrating the principal steps in the method, embodying the present invention, for forming a tubular article.
Figure 2:
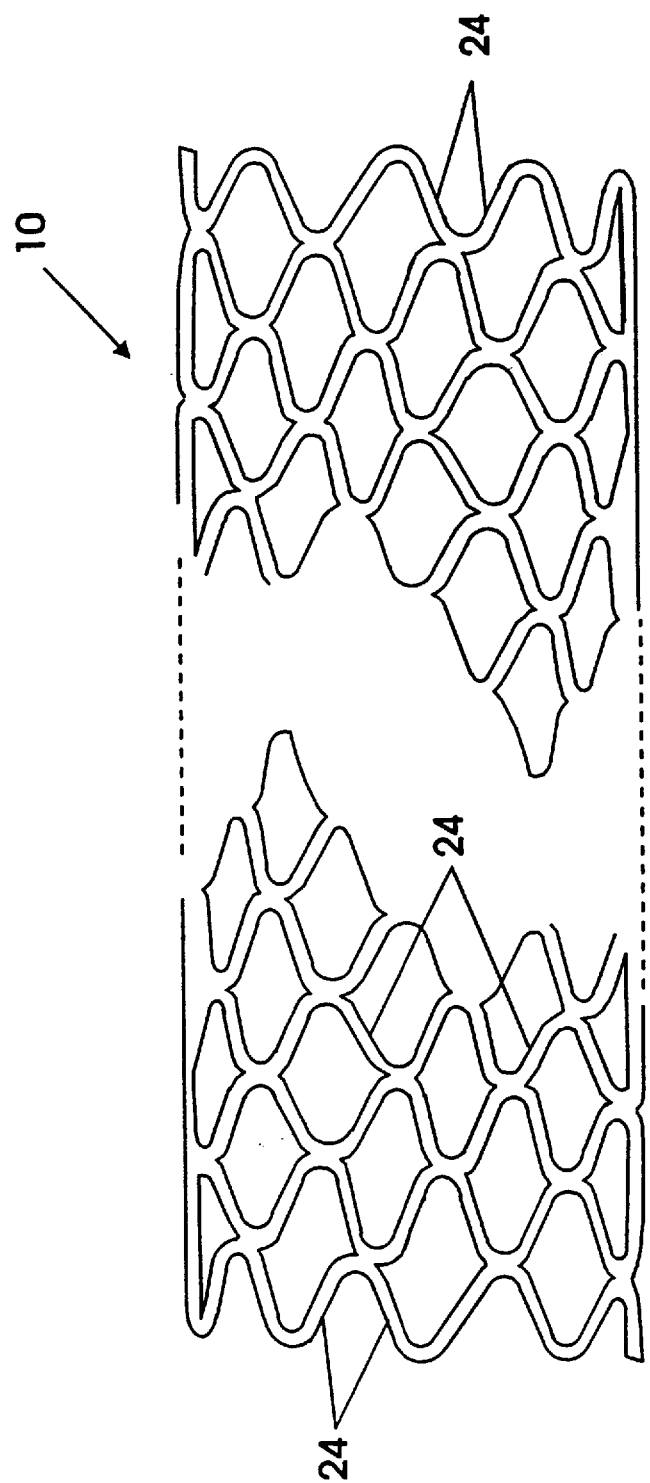
FIG. 2 is a elevational view of a stent manufactured in accordance with the method embodying the present invention.

In the preferred exemplary embodiment of the present invention, a method for forming a tubular article having a perforated annular wall, such as a stent 10 as shown in FIG. 2, includes initially providing a tubular member or cylinder, having a solid annular wall defined by an exterior cylindrical surface and an interior cylindrical surface as indicated at block 12 in FIG. 1. The tubular member is preferably formed of tantalum, stainless steel, or other metallic or non-metallic material suitable for use in the end application of the article. In the illustrative embodiment, the tubular member is a tantalum or stainless steel cylinder that is cut to a desired length and has a wall thickness of from about 5 mils to about 10 mils. Tantalum is a particularly desirable material for formation of a stent because it is readily definable by x-rays and can thus be observed during implantation.

As indicated at block 14, The tube is coated on both the exterior and interior cylindrical surface with a photoresist, such as NOVALACM. Photoresist is a light-sensitive material that is applied as a coating to a substrate, exposed as represented by block 16, and developed prior to chemical etching. The exposed areas serve as a mask for selective etching after removal of the unexposed photoresist material by rinsing in sodium hydroxide.

The coated cylindrical surfaces are then developed, as indicated at block 18, and then etched as indicated at block 20, with a suitable etchant which removes the unexposed portions of the coating and the immediate underlying portions of the solid annual wall of the tubular member. The etching process forms a series of voids, or openings, through the solid wall of the tubular member, thereby forming a perforated annular wall defined by the remaining skeletal framework that remains after etching. In the illustrative embodiment of the present invention, the exposed areas of the coating define a desired rib pattern that, after removal of the unexposed material, forms a skeletal framework, such as the stent 10. It is important that the exposed pattern on each of the surfaces of the tubular article be aligned, i.e., that the respective patterns are identical mirror images of one another and in complete registration with each other so that an exposed area on the outer cylindrical surface directly overlays an identical exposed area on the interior cylindrical surface. In the preferred exemplary embodiment, sodium hydroxide or potassium hydroxide is used as the etching agent for the tantalum tubular member.

Desirably, as indicated at block 22, the etched tubular article 10 is chemically deburred with a suitable deburring agent, such as a dilute solution of aqua regia, nitric acid, or hydrochloric acid.

Advantageously, the skeletal framework may be formed of almost any conceivable arrangement of interconnecting ribs 24 by simultaneously rotating and translating the tubular member along a longitudinal axis. An apparatus 30, as best shown in FIG. 3, specifically arranged for exposing a light-sensitive coating applied to a tubular member 32 in accordance with the above-described method, includes a means 34 for rotatably supporting the tubular member 32, such as a chuck that clamps the tubular member 32 at one end, on either the inside or outside diameter, or on both diametric surfaces. The apparatus 30 also includes a means 36 for rotating the tubular member 32 about a predetermined longitudinal axis 33, preferably the longitudinal axis of the member 32 itself. The means 36 for rotating the tubular member 32 includes a drive motor 38, such as a stepper or servomotor, operatively coupled to the means 34 for rotatably supporting the tubular member 32.

The apparatus 30 for exposing a light-sensitive coating disposed on the tubular member 32 includes a laser 40 that is optically connected to a beam splitter 42 by a fiber optic cable 44. The beam splitter 42 is desirably positioned at one end of a bifurcated optical guide 46 that has a first arm 48 extending along the longitudinal axis of the tubular member 32 and positioned adjacent the exterior cylindrical surface of the tubular member 32 when the member is rotatably supported in the apparatus 30. The bifurcated optical guide 46 also includes a second arm 50 that extends along the longitudinal axis of the tubular member 32 and is positioned adjacent the interior cylindrical surface of the tubular member 32 when the member is rotatably supported in the apparatus 30. Each of the arms 48, 50 of the optical guide 46 respectively have a head portion 52, 54, that are aligned, one with the other, and arranged to transmit a respective beam of laser energy from the beam splitter 42 to the respective head portion 52, 54. A lens 56, 58 is disposed in each of the head portions 52, 54 of the arms 48, 50. Each of the lenses 56, 58 are constructed to focus a respective beam 60, 62 of laser energy onto the respective adjacently disposed cylindrical surface of the tubular member 32 when the member 32 is rotatably mounted in the apparatus 30. Alternatively, the lenses 56, 58 may comprise a focusing mirror mounted at a 45° angle with respect to the arms 48, 50 and to the respective cylindrical surfaces of the tubular member 32.

The apparatus 30 also includes a means 64 for moving the bifurcated optical guide 46 or the tubular member 32 along the longitudinal axis 33 of the tubular member 32. In the preferred embodiment of the present invention, the means 64 for moving either the optical guide 46 or the member 32 includes a precision table 66 that has a support 68 for carrying the bifurcated optical guide 46 and the beam splitter 42. The precision table 66 is desirably moved in a linear direction by a stepper or servo motor 70, operatively coupled to the table 66 and adapted to controllably move the optical guide 46 along the longitudinal axis 33 of the tubular member 32. Desirably, the arms 48, 50 of the bifurcated optical guide 46 have a length that is at least as long as the length of the tubular member 32, so that the head portions 52, 54 of the optical guide 46 are capable of being positioned adjacent the mounted end of the tubular member 32 by insertion through the open end of the tubular member 32.

Desirably, the apparatus 30 for exposing a light-sensitive coating disposed on a tubular member 32, includes a programmable controller 72 that is operatively connected to a rotary encoder 74 that is in electrical communication with the rotary drive motor 38, and to a linear encoder 76 in electrical communication with the motor 70 that provides linear translation of the precision table 66. The controller 72 is also in direct electrical communication with the rotary drive motor 38 and the linear drive motor 70 and controls the operation of both motors 38, 70 in response to position signals received from the respective encoders 74, 76. By controlling both the rotary motion of the chuck 34 and the linear motion of the optical guide 46, almost any conceivable pattern resulting from a combination of rotary and linear displacements may be drawn, i.e., the coating exposed, on the respective cylindrical surfaces of the tubular member 32. One example of such a pattern is illustrated in FIG. 2, in which the exposed areas form the ribs 12 of the stent 10, although other arrangements, such as a single or double helical coil pattern may also be constructed. The width of ribs 12 are essentially determined by the width of the focused laser beams 60, 62. In the illustrative embodiment that laser beams 60,62 are focused to produce a circular spot having a diameter of from about 0.4 mils to about 0.7 mils, a width somewhat less than the wall thickness of the tubular member 32.

Although the present invention is described in terms of a preferred exemplary embodiment, those skilled in art will recognize that changes in the mounting arrangement of the tubular member, and relative translation of the laser beam with respect to the tubular member, may be made without departing from the spirit of the invention. For example, it may be desirable to move the tubular member 32 itself along its longitudinal axis and/or rotate the optical source about the longitudinal axis of the tubular member 32. Likewise, the openings, or perforations, in the wall of the tubular member 32 may also have other shapes and arrangements than those described and illustrated herein. Such changes are intended to fall within the scope of the following claims. Other aspects, features and advantages of the present invention may be obtained from a study of this disclosure and the drawings, along with the appended claims.

What is claimed is:

1. A method for forming a tubular article having a perforated annular wall, comprising:

providing a tubular member having a solid annular wall defined by an exterior cylindrical surface and an interior cylindrical surface;

coating the exterior and interior cylindrical surfaces of the tubular member with a photoresist;

exposing selected portions of the photoresist coated exterior and interior cylindrical surfaces to light, said selected portions on the exterior cylindrical surface of the member being in respective alignment with the selected portions on the interior cylindrical surface of the member;

developing the photoresist coating;

etching said coating and removing unexposed portions of the coating and immediate underlying portions of the solid annular wall, thereby forming a tubular article having a wall structure defined by a skeletal framework.

2. A method for forming a tubular article, as set forth in claim 1, wherein said method includes chemically deburring said skeletal framework.

3. A method for forming a tubular article, as set forth in claim 1, wherein said exposing selected portion of the photoresist coated exterior and interior cylindrical surfaces to light includes simultaneously transmitting a laser beam to said selected portions on each of said cylindrical surfaces, rotating said tubular member about a longitudinal axis, and moving each of said laser beams along said longitudinal axis.

4. An apparatus for exposing a light sensitive coating disposed on a tubular member having a longitudinal axis, an exterior cylindrical surface, an interior cylindrical surface, and spaced ends; comprising:

a means for rotatably supporting said tubular member;

a laser;

a beam splitter in optical communication with said laser;

a bifurcated optical guide in optical communication with said beam splitter and having one arm extending along said longitudinal axis and adapted to be disposed adjacent the exterior cylindrical surface of the tubular member when said member is rotatably supported in said apparatus, and a second arm extending along said longitudinal axis and adapted to be disposed adjacent the interior cylindrical surface of the tubular member when said member is rotatably supported in said apparatus, each of said arms of the optical guide having a head portion aligned with each other and arranged to transmit a respective beam of laser energy from said beam splitter to said head portion;

a lens disposed in each of said head portions of the arms of the bifurcated optical guide, each of said lens being constructed to focus said respective beam of laser energy on the respective adjacently disposed cylindrical surface of the tubular member when said member is rotatably mounted in said apparatus;

a means for rotating one of said tubular member and said bifurcated optical guide about said longitudinal axis; and a means for moving one of said bifurcated optical guide and said tubular member along said longitudinal axis.

5. An apparatus for exposing a light sensitive coating, as set forth in claim 4, wherein said means for rotatably supporting said tubular member includes a chuck adapted to clamp one end of said tubular member.

6. An apparatus for exposing a light sensitive coating, as set forth in claim 5, wherein said means for rotating said tubular member about said longitudinal axis includes an electric motor operatively connected to said chuck.

7. An apparatus for exposing a light sensitive coating, as set forth in claim 4, wherein said means for moving one of said bifurcated optical guide and said tubular member along said longitudinal axis includes a motor-driven precision table on which said optical guide is supported.

8. An apparatus for exposing a light sensitive coating, as set forth in claim 4, wherein the ends of the tubular member are spaced apart at a selected distance, and the each of the arms of the bifurcated optical guide have a length that is at least as long as said selected distance at which the ends of the tubular member are spaced apart.

9. An apparatus for exposing a light sensitive coating, as set forth in claim 4, wherein said apparatus includes a controller operatively connected to said means for rotating said tubular member about said longitudinal axis and to said means for moving said bifurcated optical guide along said longitudinal axis.

* * * * *

UNITED STATES PATENT AND TRADEMARK OFFICE
CERTIFICATE OF CORRECTION

PATENT NO. : 5,855,802
DATED : Jan. 5, 1999
INVENTOR(S) : Acciai et al.

It is certified that error appears in the above-identified patent and that said Letters Patent is hereby corrected as shown below:

Column 3, line 20, delete "NOVALACM" change to -- NOVALAC$^{TM}$ --.

Signed and Sealed this

First Day of June, 1999

Attest:

Q. TODD DICKINSON

*Attesting Officer*     *Acting Commissioner of Patents and Trademarks*